US012678055B2

(12) United States Patent
Hibino et al.

(10) Patent No.: US 12,678,055 B2
(45) Date of Patent: Jul. 14, 2026

(54) HEADSET

(71) Applicant: FOSTER ELECTRIC COMPANY, LIMITED, Tokyo (JP)

(72) Inventors: Yo Hibino, Akishima (JP); Yasuo Kawana, Akishima (JP)

(73) Assignee: FOSTER ELECTRIC COMPANY, LIMITED, Tokyo (JP)

( * ) Notice: Subject to any disclaimer, the term of this patent is extended or adjusted under 35 U.S.C. 154(b) by 652 days.

(21) Appl. No.: 18/246,844

(22) PCT Filed: Sep. 28, 2021

(86) PCT No.: PCT/JP2021/035587
§ 371 (c)(1),
(2) Date: Mar. 27, 2023

(87) PCT Pub. No.: WO2022/071299
PCT Pub. Date: Apr. 7, 2022

(65) Prior Publication Data
US 2023/0363649 A1 Nov. 16, 2023

(30) Foreign Application Priority Data

Sep. 30, 2020 (JP) ................................. 2020-164729

(51) Int. Cl.
*A61B 5/01* (2006.01)
*A61B 5/00* (2006.01)
(Continued)

(52) U.S. Cl.
CPC .............. *A61B 5/01* (2013.01); *A61B 5/6817* (2013.01); *G01K 13/20* (2021.01); *H04R 1/08* (2013.01)

(58) Field of Classification Search
CPC ........ A61B 5/01; A61B 5/6817; G01K 13/20; G01K 11/24; H04R 1/08; H04R 3/005; H04R 1/1016; H04R 1/028; G01H 5/00
See application file for complete search history.

(56) References Cited

U.S. PATENT DOCUMENTS 10,016,162 B1 * 7/2018 Rogers ................... G01J 5/0011
10,491,981 B1 * 11/2019 Wang ................... H04R 1/1041
(Continued)

FOREIGN PATENT DOCUMENTS

CA 3236086 A1 * 7/2016 ......... A61B 5/14546
CA 3090916 A1 * 8/2019 ............... A61B 7/00
(Continued)

OTHER PUBLICATIONS

Search Report and Written Opinion in International Application No. PCT/JP2021/035587 dated Dec. 21, 2021, 8 pages.

*Primary Examiner* — Jeffrey G. Hoekstra
(74) *Attorney, Agent, or Firm* — MARSHALL, GERSTEIN & BORUN LLP

(57) ABSTRACT

A headset includes: a hollow housing (10) to be worn at an ear of a user; a cylindrical ear canal insertion part (12) that is a portion of the housing (10), and that is provided at a portion of the housing (10) at a side of an ear canal; a driver (14) for signal output, provided at an interior of the housing (10); a microphone (18) provided so as to collect a signal propagating at a second hollow part (16A), extending from inside an ear canal insertion part (12) and different from a first hollow part (12A) inside the ear canal insertion part (12), through which a signal output from the driver (14) propagates; and a computation unit (22) configured to measure a temperature inside the ear canal based on a collected signal collected by the microphone (18) at a time when a measurement signal is output from the driver (14).

10 Claims, 19 Drawing Sheets

(51) Int. Cl.
    *G01K 13/20*         (2021.01)
    *H04R 1/08*         (2006.01)

(56)               References Cited

U.S. PATENT DOCUMENTS

| | | | |
|---|---|---|---|
| 10,659,867 B2 * | 5/2020 | Petrank | H04R 29/001 |
| 11,042,617 B2 * | 6/2021 | Lesso | H04R 1/1041 |
| 11,122,350 B1 * | 9/2021 | Lesso | H04R 3/005 |
| 11,178,478 B2 * | 11/2021 | Petrank | H04R 29/001 |
| 11,438,683 B2 * | 9/2022 | Gong | G06F 21/84 |
| 11,480,547 B2 * | 10/2022 | Phan Le | G01F 23/2961 |
| 11,962,966 B2 * | 4/2024 | Park | H05K 1/181 |
| 2014/0233749 A1 | 8/2014 | Shimizu et al. | |
| 2015/0023542 A1 | 1/2015 | Shimizu | |
| 2017/0003176 A1 | 1/2017 | Phan Le et al. | |
| 2017/0347180 A1 | 11/2017 | Petrank | |
| 2020/0275187 A1 * | 8/2020 | Petrank | G10L 25/51 |
| 2024/0183722 A1 * | 6/2024 | Hibino | G01K 1/16 |

FOREIGN PATENT DOCUMENTS

| | | | | |
|---|---|---|---|---|
| CA | 2877717 C | * | 1/2022 | A61B 1/04 |
| EP | 1475035 A1 | * | 11/2004 | G01J 5/08 |
| EP | 3081155 A1 | * | 10/2016 | G16H 40/63 |
| JP | 2008/136556 A | | 6/2008 | |
| JP | 2012-047628 A | | 3/2012 | |
| JP | 2014-187679 A | | 10/2014 | |
| JP | 2015-023495 A | | 2/2015 | |
| JP | 2019-523581 A | | 8/2019 | |
| KR | 102408691 B1 | * | 6/2022 | A61B 5/0261 |

* cited by examiner

FIG.2

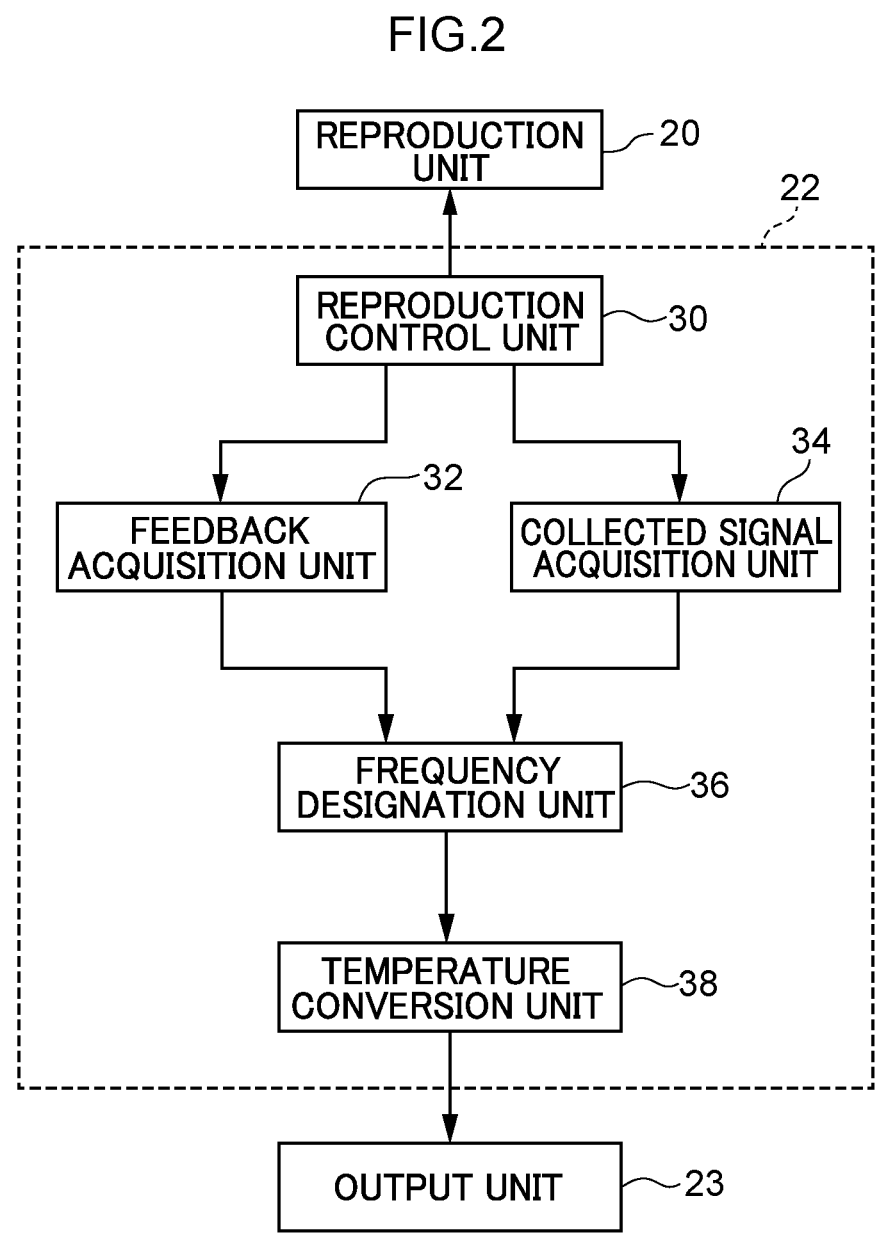

```
        ┌──────────────────┐
        │  REPRODUCTION    │─── 20
        │      UNIT        │
        └──────────────────┘
                 ▲
    ┌────────────│─────────────────────────────── 22
    │            │                               │
    │   ┌──────────────────┐                     │
    │   │  REPRODUCTION    │─── 30               │
    │   │  CONTROL UNIT    │                     │
    │   └──────────────────┘                     │
    │       │          │                         │
    │       ▼          ▼                         │
    │ ┌───────────┐  ┌──────────────────┐  34    │
    │ │ FEEDBACK  │32│ COLLECTED SIGNAL │        │
    │ │ACQUISITION│  │ ACQUISITION UNIT │        │
    │ │   UNIT    │  └──────────────────┘        │
    │ └───────────┘          │                   │
    │       │                │                   │
    │       ▼                ▼                   │
    │   ┌──────────────────────┐                 │
    │   │     FREQUENCY        │─── 36           │
    │   │ DESIGNATION UNIT     │                 │
    │   └──────────────────────┘                 │
    │              │                             │
    │              ▼                             │
    │   ┌──────────────────────┐                 │
    │   │    TEMPERATURE       │─── 38           │
    │   │  CONVERSION UNIT     │                 │
    │   └──────────────────────┘                 │
    │              │                             │
    └──────────────│─────────────────────────────┘
                   ▼
        ┌──────────────────┐
        │   OUTPUT UNIT    │─── 23
        └──────────────────┘
```

FIG.18
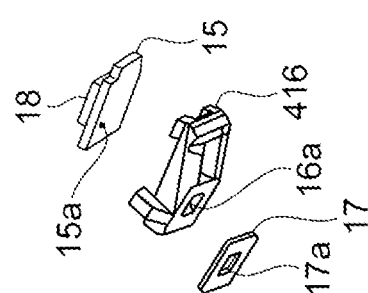
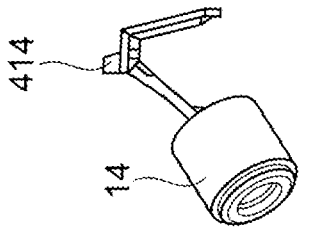
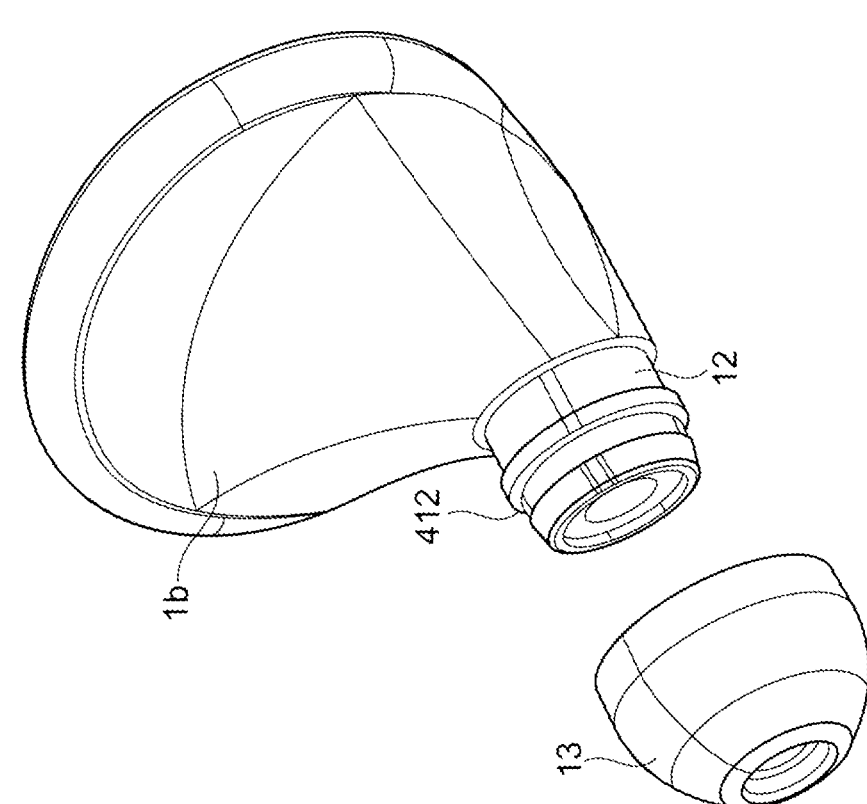

HEADSET

TECHNICAL FIELD

The technique of the present disclosure relates to head-sets.

BACKGROUND ART

Conventionally, earplug-type thermometers using thermopiles, thermistor sensors, and infrared sensors are known.

For example, earphone devices are known that are characterized by having at least two of an acoustic speaker for amplified output of an acoustic signal, body temperature detection means for detecting the body temperature of a human body by an infrared method, and pulse detection means for optically detecting the pulsation of blood flowing through the blood vessels of a human body housed in a case and integrated (Japanese Patent Application Laid-Open No. 2008-136556).

SUMMARY OF THE INVENTION

Problem to be Solved by the Invention

In an earphone type temperature detection method, while it would be conceivable to detect three temperatures—namely, those of the eardrum, the skin, and the air—a contact format or the like blocks the front of an earphone driver. Further, because the external auditory canal is curved, it is difficult to dispose the sensor at a position at which the temperature of the eardrum can be taken, and physical compatibility with earphones is difficult.

Further, temperature sensors such as thermopiles and thermistors for detecting temperature are expensive. In the technique described in Patent Document 1 noted above, it is necessary to add an infrared sensor to the earphone, and there are concerns regarding cost.

Further, since the above-mentioned temperature sensors and the like detect absolute temperature, the sensors themselves have temperature characteristics. Since temperature is converted into an electric signal, variations due to individual differences occur.

In consideration of the foregoing circumstances, the technique of the present disclosure aims to provide a headset capable of accurately measuring temperature with a simple configuration.

Means for Solving the Problem

One aspect of the present disclosure is a headset that includes: a hollow housing to be worn at an ear of a user; a cylindrical ear canal insertion part that is a portion of the housing, and that is provided at a portion of the housing at a side of an ear canal; a driver for signal output, provided at an interior of the housing; a first hollow part provided inside the ear canal insertion part, through which a signal output from the driver propagates; a second hollow part that is different from the first hollow part, extending from inside the ear canal insertion part; a microphone provided so as to collect a signal propagating at the second hollow part; and a computation unit configured to measure a temperature inside the ear canal based on a collected signal collected by the microphone at a time at which a measurement signal is output from the driver.

Effect of the Invention

According to one aspect of the present disclosure, by measuring the temperature in the ear canal based on the collected sound signals collected by the microphone when a measurement signal is output from the driver, with a simple configuration, the temperature can be measured with high accuracy.

BRIEF EXPLANATION OF THE DRAWINGS

FIG. 2 is a block diagram showing a computation unit of the headset according to the first embodiment of the technique of the present disclosure.

FIG. 18 is an exploded perspective view of the driver, microphone and front housing portions in the example.

BEST MODE FOR CARRYING OUT THE INVENTION

Figure 1:
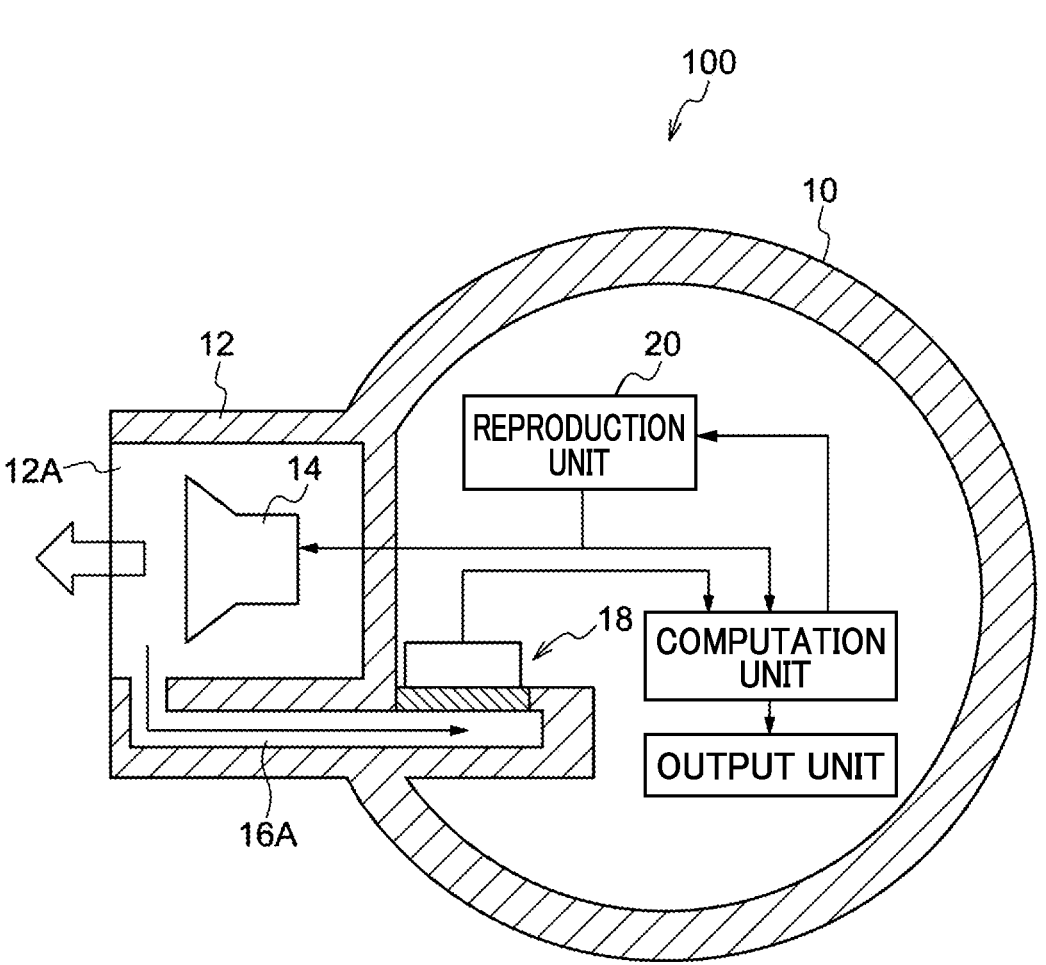
FIG. 1 is a cross-sectional view showing the overall configuration of a headset according to a first embodiment of the technique of the present disclosure.

Hereinafter, embodiments of the technique of the present disclosure will be described in detail with reference to the drawings.

Outline of Embodiments of Technique of Present Disclosure

In embodiments of the technique of the present disclosure, the temperature of the external auditory canal (ear canal) space is measured from the delay time generated when sound produced by a sound generator (earphone driver) passes through a space connected to the ear canal.

For example, when the length l of the path along which sound passes is 6 mm and the temperature of the ear canal space is 25° C., a delay of 17.34 μsec occurs between the sound generator and a sound collection sensor. Further, this delay time is temperature dependent.

When the length l of the path along which the sound passes is 6 mm, the speed of sound V when the temperature is t° C. is V=331+0.6t [m/s], and therefore, a temperature rise of 1° C. shortens the delay time by approximately 0.03 μsec. That is, if the delay time can be accurately measured, the temperature can be determined.

However, these minute differences in delay time cannot be determined after digital processing. This is because in a case in which the length l of the path along which the sound passes is 6 mm, the resolution required to determine the accuracy required for a thermometer (0.1° C.) is 0.003 μsec; however, the minimum unit that can be handled after digital processing is one sample period (10.4 μsec at 96 kHz).

Therefore, in the present embodiment, in order to accurately measure in nanoseconds the time it takes for a reproduced sound to pass through a space of length l [mm] connected to the ear canal and be picked up by a microphone, acoustic signals collected along two paths are compared and the delay time calculated. The difference between these "two routes" also includes whether or not the "space of length l [mm] connected to the ear canal" is passed through unnecessarily.

Moreover, the following three methods are used as a method of calculating the delay time.

In the first method, a signal (for example, a sine wave) that changes at a specific frequency is used to compare the phases of acoustic signals collected by two systems. At this time, the frequency at which a delay of half a wavelength or more due to the "space of length l [mm] connected to the ear canal" has the same phase or the opposite phase is specified. Then, conversion to temperature is performed using a table or formula storing the correlation between frequency and temperature measured or simulated in advance in a similar system.

In the second method, sound signals of two systems collected using a signal that changes at a specific frequency are added or subtracted, and cancelled frequency bands are determined. At this time, two sound signals from the observed acoustic signals are added or subtracted and the minimum or maximum frequency, or the estimated minimum or maximum frequency, is specified. Further, conversion to temperature is performed using a table or formula storing the correlation between frequency and temperature measured or simulated in advance in a similar system.

In the third method, the collected sound signals of the two systems are added or subtracted, and frequency analysis is used to determine which frequency bands are cancelled.

Further, conversion to temperature is performed using a table or formula storing the correlation between frequency and temperature measured or simulated in advance in a similar system.

Configuration of Headset According to First Embodiment of Technique of Present Disclosure As shown in FIG. 1, a headset 100 according to the first embodiment of the technique of the present disclosure has a hollow housing 10 that is worn at a user's ear and that contains various functional components inside. The headset 100 also has a cylindrical ear canal insertion part 12 having a first hollow portion 12A that is one portion of the housing 10 and that is provided at a part on the ear canal side of the housing 10 when worn at the user's ear.

Further, the headset 100 has a driver 14 for signal output provided inside the housing 10.

Further, the housing 10 has a second hollow portion 16A extending from inside the ear canal insertion portion 12 that is a different hollow portion from the first hollow portion 12A propagating inside the ear canal insertion portion 12.

Further, the headset 100 includes a microphone 18 provided so as to collect a signal propagating in the second cavity 16A, a reproduction unit 20 that outputs a signal for measurement from the driver 14, a computation unit 22 that measures the temperature inside the ear canal based on a signal collected by the microphone 18 when the measurement signal is output from the driver 14, and an output unit 23 that outputs a measurement result obtained by the computation unit 22. In the present embodiment, a microphone 18 is provided to collect signals propagating through the second hollow portion 16A extending from within the ear canal insertion portion 12 having the first hollow portion 12A, and the microphone 18 is arranged rearward of the driver 14.

The reproduction unit 20, the computation unit 22, and the output unit 23 are mounted on a printed wiring board (not shown) arranged inside the housing 10.

The computation unit 22 measures the temperature inside the ear canal based on the measurement signal output from the driver 14 and the signal collected by the microphone 18.

Specifically, the computation unit 22 functionally includes, as shown in FIG. 2, a reproduction control unit 30, a feedback acquisition unit 32, a collected sound signal acquisition unit 34, a frequency designation unit 36 and a temperature conversion unit 38.

Figure 3:
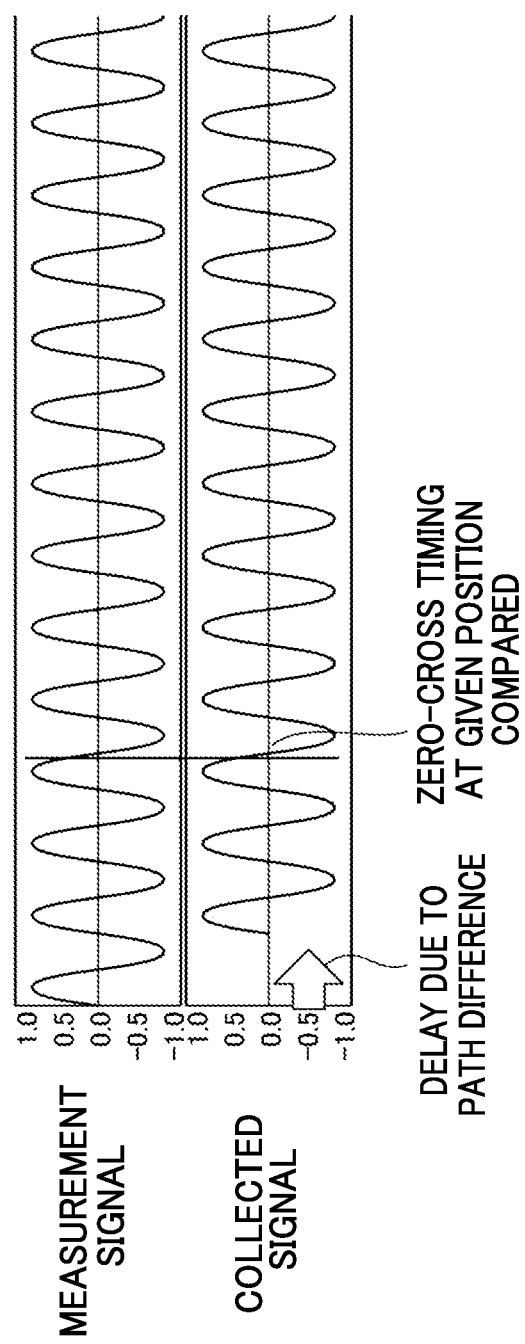
FIG. 3 is a diagram showing an example of a measurement signal and a collected sound signal using a sine wave.
Figure 4:
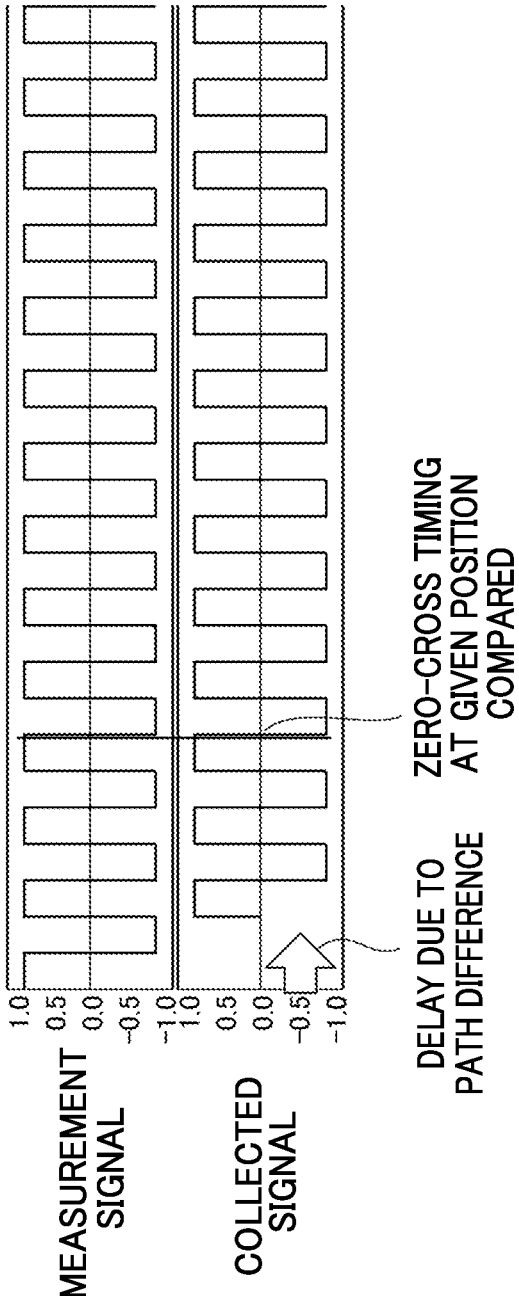
FIG. 4 is a diagram showing an example of a measurement signal and a collected sound signal using rectangular waves.

The reproduction control unit 30 controls the reproduction unit 20 such that measurement signals that change at each of plural predetermined frequencies are sequentially output from the driver 14. For example, the reproduction control unit 30 causes the driver 14 to output a measurement signal using a sine wave as shown in FIG. 3. Alternatively, the reproduction control unit 30 causes the driver 14 to output a measurement signal using a rectangular wave as shown in FIG. 4. Although FIGS. 3 and 4 show an example using a measurement signal having a single frequency, a measurement signal with a sweeping frequency may be used.

Figure 5:
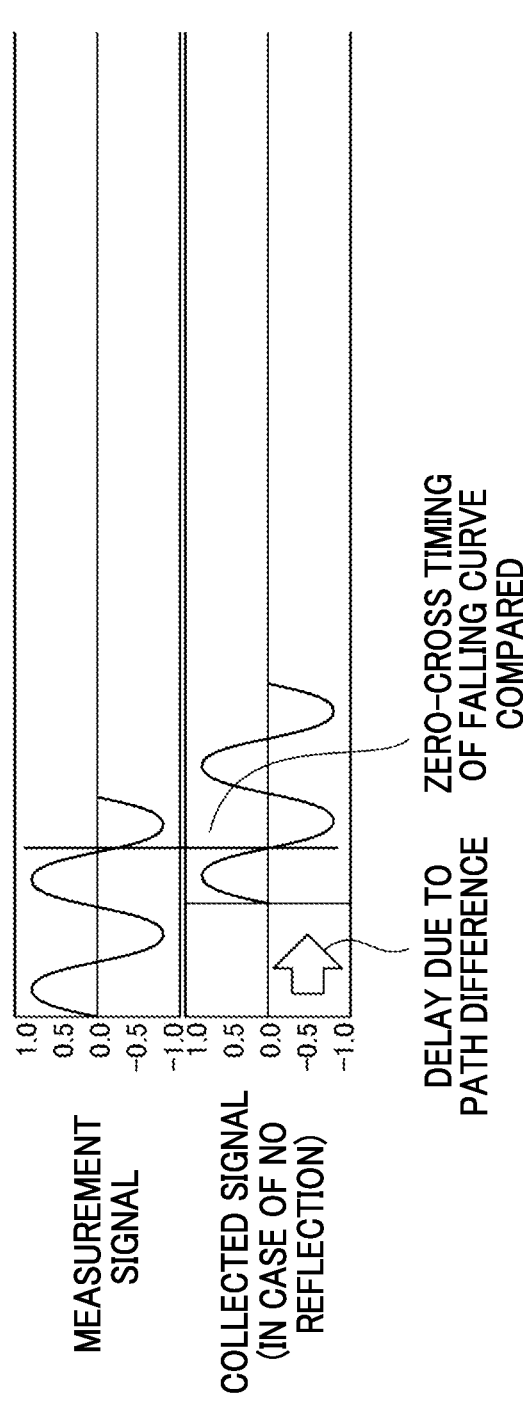
FIG. 5 is a diagram showing an example of a measurement signal and a collected sound signal using a single-shot sine wave.

In a case in which the reflected sound in the ear canal is large, the reproduction control unit 30 causes the driver 14 to output a measurement signal using a single-shot wave such as a two-cycle sine wave as shown in FIG. 5. Since sound reflected at the ear canal may return to the microphone 18 depending on the structure of the headset 100, by using a single-shot measurement signal in this way, comparison of zero-cross timings, which is described below, can be performed without being affected by sound reflected at the ear canal.

Further, as the plural frequencies, frequencies from 10.2 kHz to 10.6 kHz determined at intervals of 2 Hz may be used, for example. In other words, in a case in which the range used as the measurement signal is from 10.2 kHz to 10.6 kHz, since it is necessary to change the frequency every 2 Hz in order to measure with a resolution of 0.1° C., the frequency of the measurement signal is changed every 2 Hz.

The feedback acquisition unit 32 acquires the measurement signal output from the reproduction unit 20 to the driver 14. Specifically, the feedback acquisition unit 32 acquires the measurement signal output from the reproduction unit 20 to the driver 14 via the same transmission system (for example, a DA conversion circuit and an AD conversion circuit) as the transmission system through which signals pass in the reproduction unit 20, the driver 14, the microphone 18, and the collected sound signal acquisition unit 34.

The collected sound signal acquisition unit 34 acquires the collected sound signal collected by the microphone 18.

The frequency designation unit 36 specifies a frequency at which the measurement signal acquired by the feedback acquisition unit 32 and the collected sound signal acquired by the collected sound signal acquisition unit 34 have a relationship that corresponds to an in-phase correlation, from among plural predetermined frequencies.

For example, as shown in FIG. 3 described above, for each measurement signal and sound collection signal for which delays occur owing to differences in path, zero-cross timings at which zero-crossing occurs at given locations (for example, zero-cross timings at falling wave portions) are compared.

Figure 6:
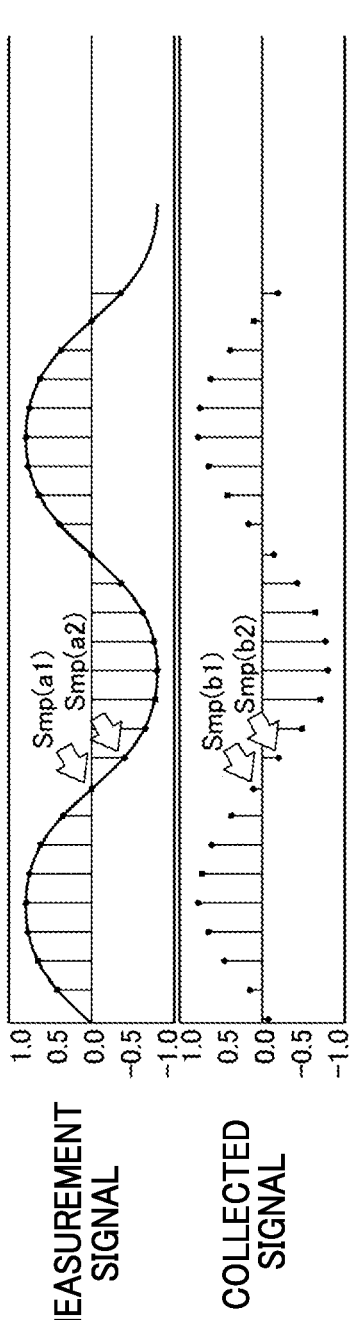
FIG. 6 is a diagram for explaining a method of estimating zero-cross timing.

In addition, since it is assumed that there is a volume difference between the measurement signal and the collected sound signal, if a zero-cross timing cannot be detected, samples before and after the zero crossing are used to estimate the zero-cross timing as shown in FIG. 6.

For example, a zero-cross timing Tzc estimated in the measurement signal is represented by the following approximation.

$$Tzc=a1/(a2-a1)$$

Here, a1 is the audio level of the sample immediately before the zero-cross timing, and a2 is the audio level of the sample immediately after the zero-cross timing.

The zero-cross timing estimated for the collected sound signal is also calculated by a similar approximation (b1/(b2−b1)).

In a case in which the absolute value of the difference in zero-cross timing between the measurement signal and the collected sound signal is equal to or less than a threshold value, it is determined that the signals are in-phase.

Figure 7:
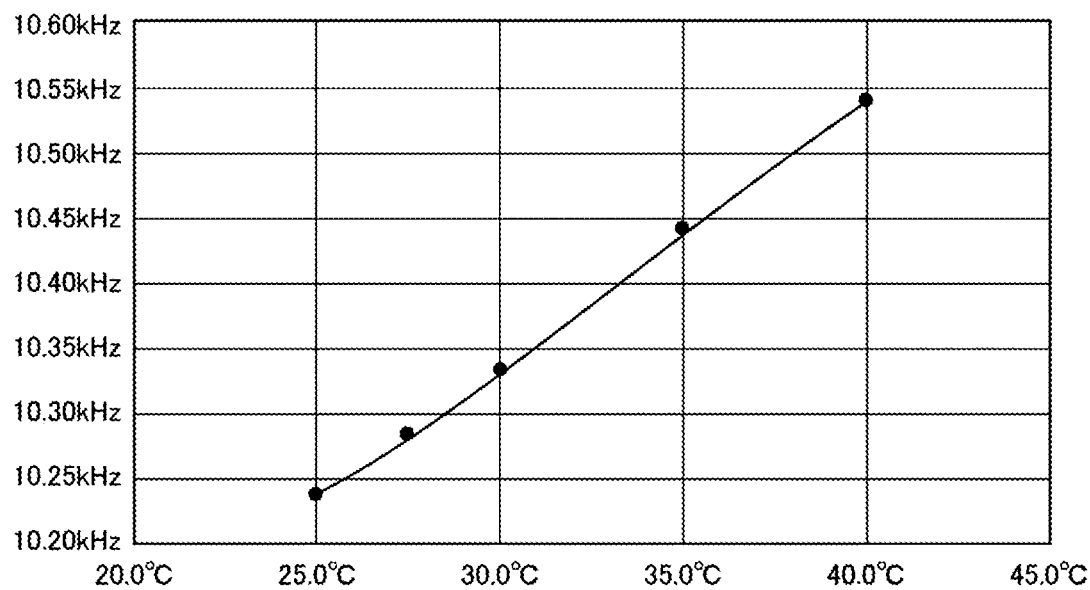
FIG. 7 is a graph showing an example of a correlation between temperature and a specified frequency.

The temperature conversion unit 38 measures the temperature in the ear canal from the specified frequency using the correlation between the frequency and the temperature obtained in advance. For example, as shown in FIG. 7, the temperature corresponding to the specified frequency is taken as the measurement result of the temperature in the ear canal from the correlation between the temperature and the frequency obtained experimentally in advance. The correlation between temperature and frequency is obtained in advance by reproducing the measurement signal for each frequency in states in which the temperature is known, and plotting differences in timing at which zero-cross points occur between the measurement signal and the collected sound signal for each temperature.

The temperature conversion unit 38 outputs the temperature measurement result via the output unit 23. For example, the temperature measurement result is transmitted to another terminal by wireless communication.

Figure 8:
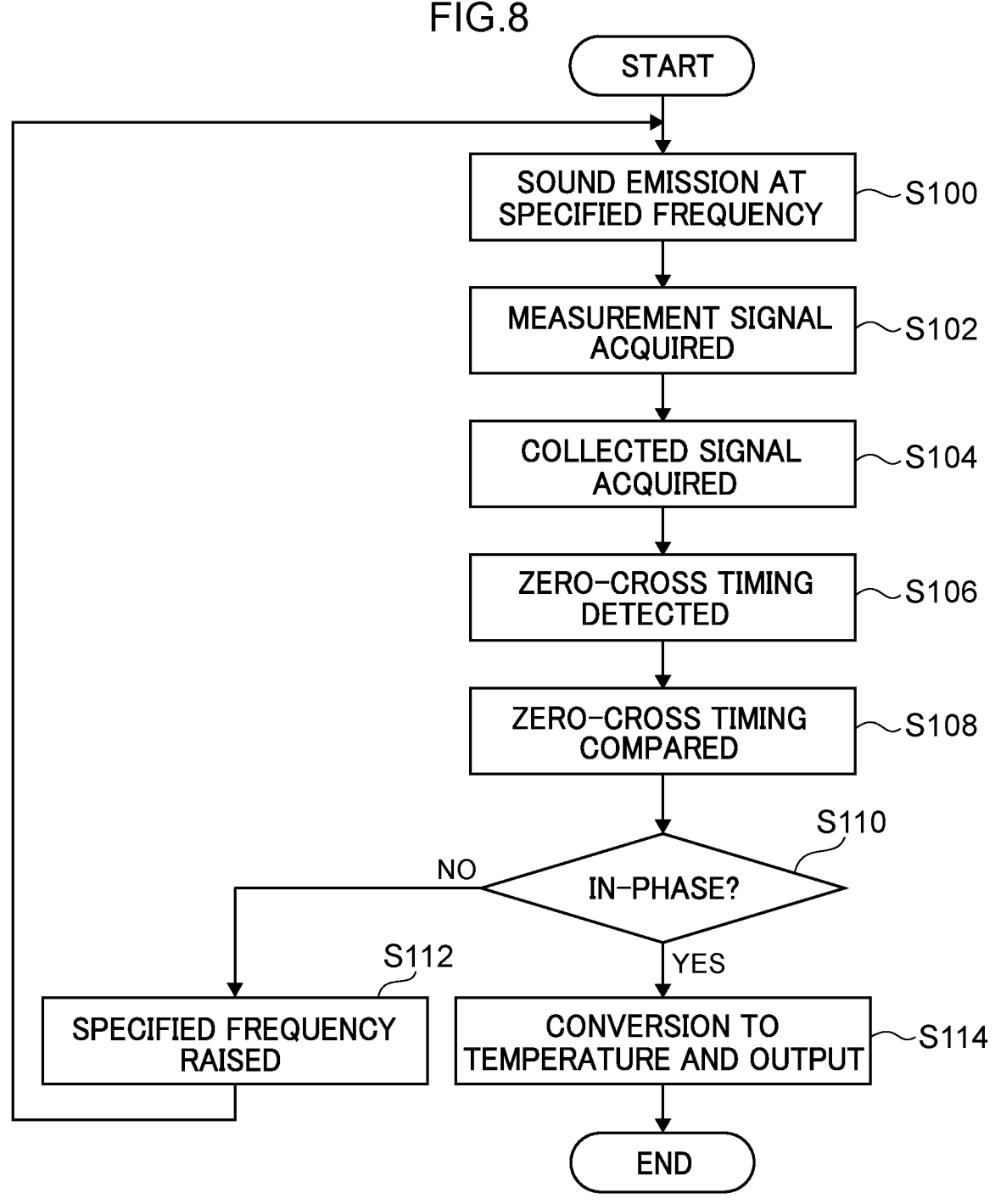
FIG. 8 is a flow chart showing details of temperature measurement processing by the headset according to the first embodiment of the technique of the present disclosure.

Operation of Headset According to First
Embodiment of Technique of Present Disclosure When the housing 10 of the headset 100 is worn at the user's ear and an instruction for temperature measurement is received from the user's terminal (not shown) by wireless communication, temperature measurement processing as shown in FIG. 8 is executed by the computation unit 22.

First, in step S100, the reproduction unit 20 is controlled such that a measurement signal that changes at any one of plural predetermined frequencies is output from the driver 14. In the present embodiment, in the first instance of step S100, the lowest frequency is selected from the plural frequencies.

In step S102, the feedback acquisition unit 32 acquires the measurement signal output from the reproduction unit 20 to the driver 14.

In step S104, the collected sound signal acquisition unit 34 acquires the collected sound signal collected by the microphone 18.

In step S106, the frequency designation unit 36 detects zero-cross timing at a given location for each of the measurement signal acquired by the feedback acquisition unit 32 and the collected sound signal acquired by the collected sound signal acquisition unit 34.

In step S108, if the absolute value of the difference in zero-cross timing between the measurement signal and the collected sound signal detected in step S106 is equal to or less than a threshold value, the frequency designation unit 36 determines that the signals are in-phase, and if it is larger than the threshold value, determines that they are out of phase.

In step S110, the frequency designation unit 36 determines whether or not the signals have been determined to be in-phase, and if they have been determined to be in-phase, the processing proceeds to step S114, and if, on the other hand, it has been determined that they are out of phase, the processing proceeds to step S112.

In step S112, a frequency that is one increment higher among the plural frequencies is set as the frequency of the measurement signal. Then, steps S100 to S110 are repeated.

In step S114, the temperature conversion unit 38 measures the temperature in the ear canal from the frequencies determined to be in-phase in step S108 described above, using the correlation between the frequency and the temperature obtained in advance.

The temperature conversion unit 38 outputs the temperature measurement result via the output unit 23, and terminates the temperature measurement processing.

As explained above, the headset according to the first embodiment of the technique of the present disclosure measures the temperature inside the ear canal based on the collected sound signal collected by the microphone when a measurement signal is output from the driver, and on the measurement signal. As a result, it is possible to measure the temperature in the ear canal with high accuracy with a simple configuration.

In addition, by disposing the microphone behind the driver, it is possible to reduce the influence of sound reflected from the eardrum, and since it is easy to separate the sound from the driver and the reflected sound from the ear canal, the temperature in the ear canal can be measured with high accuracy.

In addition, in the above-described embodiment, a frequency at which the measurement signal acquired by the feedback acquisition unit 32 and the collected sound signal acquired by the collected sound signal acquisition unit 34 have a relationship that corresponds to an antiphase correlation may be specified and, from the specified frequency, using a pre-determined correlation between frequency and temperature, the temperature in the ear canal may be measured. For example, in a case in which the absolute value of a difference between the zero-cross timing difference between the measurement signal acquired by the feedback acquisition unit 32 and the collected sound signal acquired by the collected sound signal acquisition unit 34, and ½ of the period corresponding to the frequency, is equal to or below a threshold value, it may be determined that the signals are in antiphase.

Further, the frequency designation unit 36 may, from among the plural frequencies, specify the frequency at which a value obtained by subtracting the measurement signal output from the driver 14 and the signal collected by the microphone 18 is minimized. Further, the temperature conversion unit 38 may measure the temperature in the ear canal from the specified frequency using a pre-determined correlation between frequency and temperature.

Figure 9:
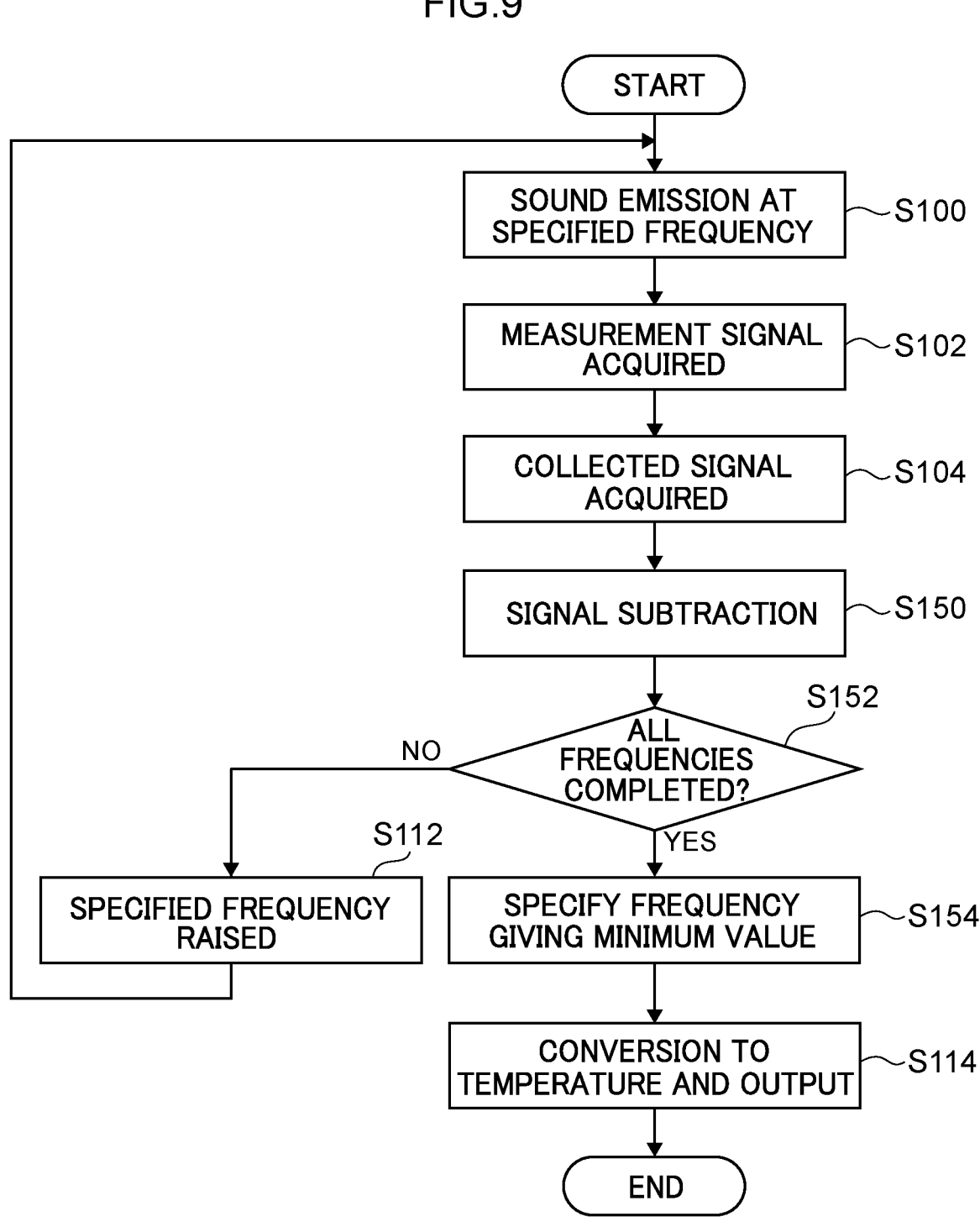
FIG. 9 is a flowchart showing details of temperature measurement processing by a headset according to another example of the first embodiment of the technique of the present disclosure.

In this case, temperature measurement processing as shown in FIG. 9 is executed by the computation unit 22. Here, the same reference numerals are assigned to the same processes as the temperature measurement processing shown in FIG. 8, and detailed description thereof is omitted.

First, in step S100, the reproduction unit 20 is controlled such that a measurement signal that changes at any one of plural predetermined frequencies is output from the driver 14.

In step S102, the feedback acquisition unit 32 acquires the measurement signal output from the reproduction unit 20 to the driver 14.

In step S104, the collected sound signal acquisition unit 34 acquires the collected sound signal collected by the microphone 18.

In step S150, the frequency designation unit 36 calculates a signal obtained by subtracting the collected sound signal acquired by the collected sound signal acquisition unit 34 from the measurement signal acquired by the feedback acquisition unit 32.

In step S152, the frequency designation unit 36 determines whether or not the respective processing of the above-described steps S100, S102, S104 and S150 has been executed with all of the plural frequencies as the frequency of the measurement signal. In a case in which the above-described steps S100, S102, S104 and S150 have been executed with all of the plural frequencies as the frequency of the measurement signal, the processing proceeds to step S154. However, in a case in which there is a frequency among the plural frequencies for which the processing of steps S100, S102, S104 and S150 has not been performed, the processing proceeds to step S112.

In step S112, a frequency that is one increment higher among the plural frequencies is set as the frequency of the measurement signal.

In step S154, the frequency designation unit 36 specifies the frequency among the plural frequencies at which the signal of the subtraction result is minimized based on the signal of the subtraction result calculated in step S150.

In step S114, the temperature conversion unit 38 measures the temperature in the ear canal from the frequency specified in step S154 described above, using the correlation between the frequency and the temperature obtained in advance, outputs the temperature measurement result via the output unit 23, and terminates the temperature measurement processing.

Further, the frequency designation unit 36 may specify, among plural frequencies, the frequency at which the sum of the measurement signal output from the driver 14 and the collected sound signal collected by the microphone 18 is maximized. Further, the temperature conversion unit 38 may measure the temperature in the ear canal from the specified frequency using a pre-determined correlation between frequency and temperature.

Configuration of Headset According to Second Embodiment of Technique of Present Disclosure Next, a headset according to a second embodiment will be described. Parts having the same configuration as in the first embodiment are denoted by the same reference numerals, and descriptions thereof are omitted.

The second embodiment differs from the first embodiment in that the temperature in the ear canal is measured using collected sound signals collected by plural microphones.

Figure 10:
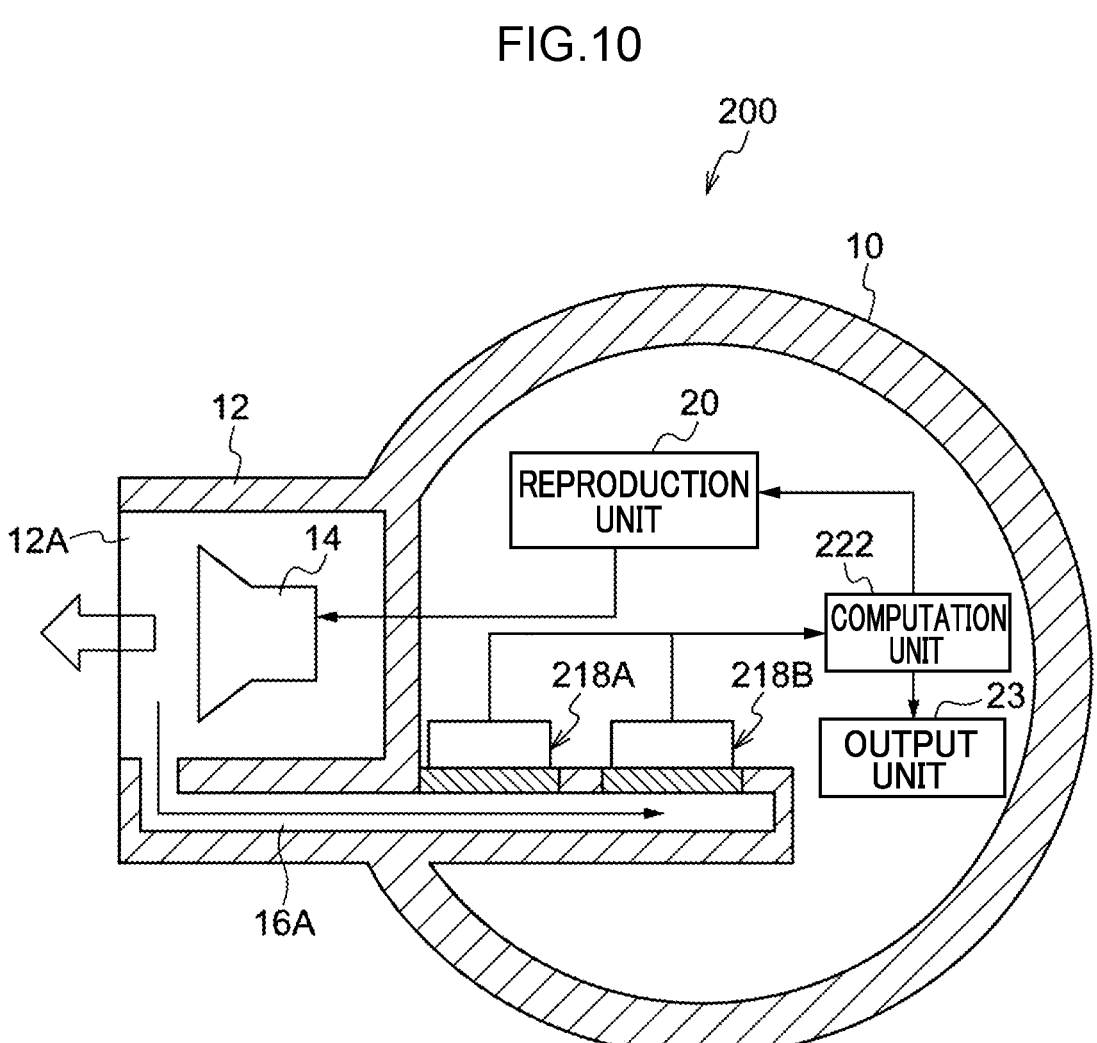
FIG. 10 is a cross-sectional view showing the overall configuration of a headset according to a second embodiment of the technique of the present disclosure.

As shown in FIG. 10, a headset 200 according to the second embodiment of the technique of the present disclosure is provided with two microphones 218A, 218B provided at different positions to collect signals propagating through the second cavity 16A, and a computation unit 222 that measures the temperature inside the ear canal based on signals collected by the microphones 218A, 218B when the measurement signal is output from the driver 14.

The computation unit 222 measures the temperature inside the ear canal based on the collected sound signals collected by the microphones 218A, 218B.

Figure 11:
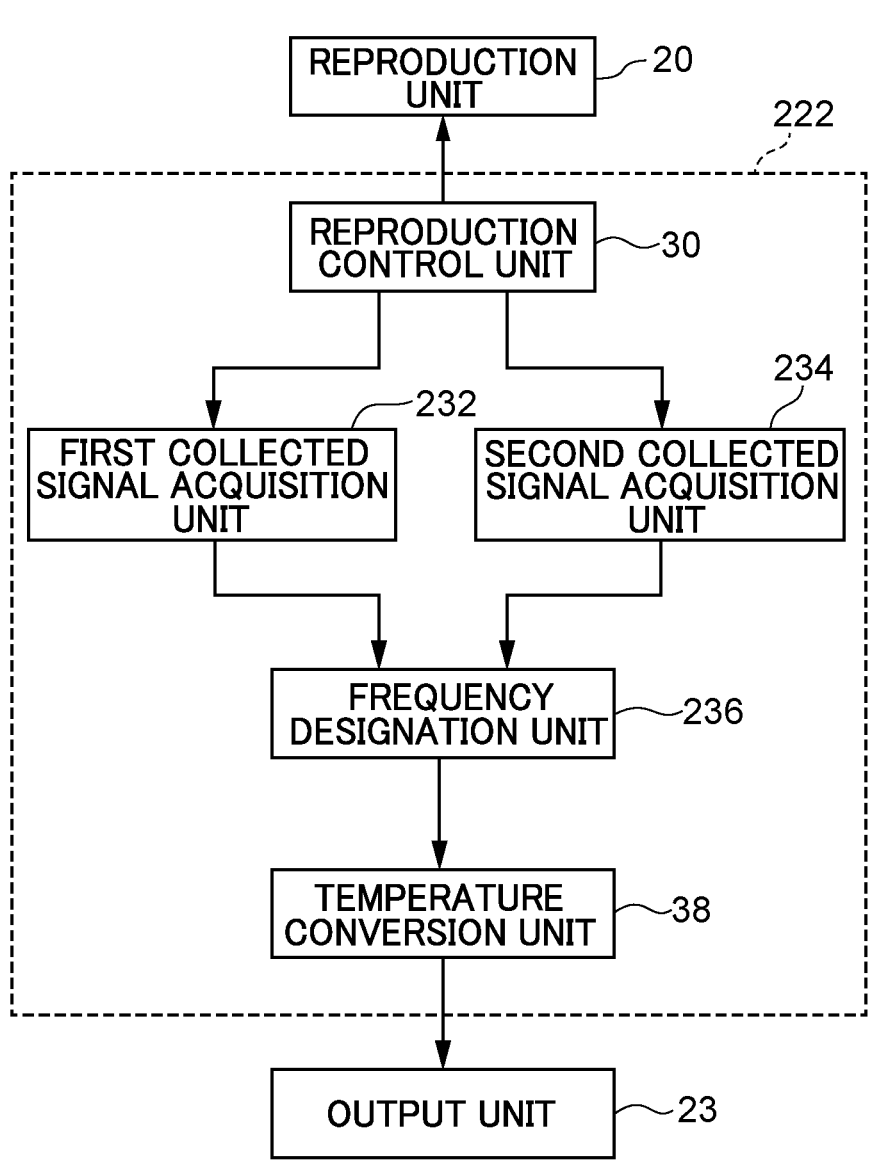
FIG. 11 is a block diagram showing a computation unit of the headset according to the second embodiment of the technique of the present disclosure.

Specifically, the computation unit 222 functionally includes, as shown in FIG. 11, a reproduction control unit 30, a first collected sound signal acquisition unit 232, a second collected sound signal acquisition unit 234, a frequency designation unit 236, and a temperature conversion unit 38.

The first collected sound signal acquisition unit 232 acquires the collected sound signal collected by the microphone 218A.

The second collected sound signal acquisition unit 234 acquires the collected sound signal collected by the microphone 218B.

The frequency designation unit 236 specifies a frequency at which the collected sound signal acquired by the first collected sound signal acquisition unit 232 and the collected sound signal acquired by the second collected sound signal acquisition unit 234 have a relationship that corresponds to an in-phase correlation from among plural predetermined frequencies.

For example, similarly to FIG. 3 above, for each of two collected sound signals in which delays occur owing to differences in path length, zero-cross timings at given locations (for example, zero-cross timings at falling wave portions) are compared. In a case in which the absolute value of the difference in zero-cross timing is equal to or less than a threshold value, it is determined that the signals are in-phase.

Figure 12:
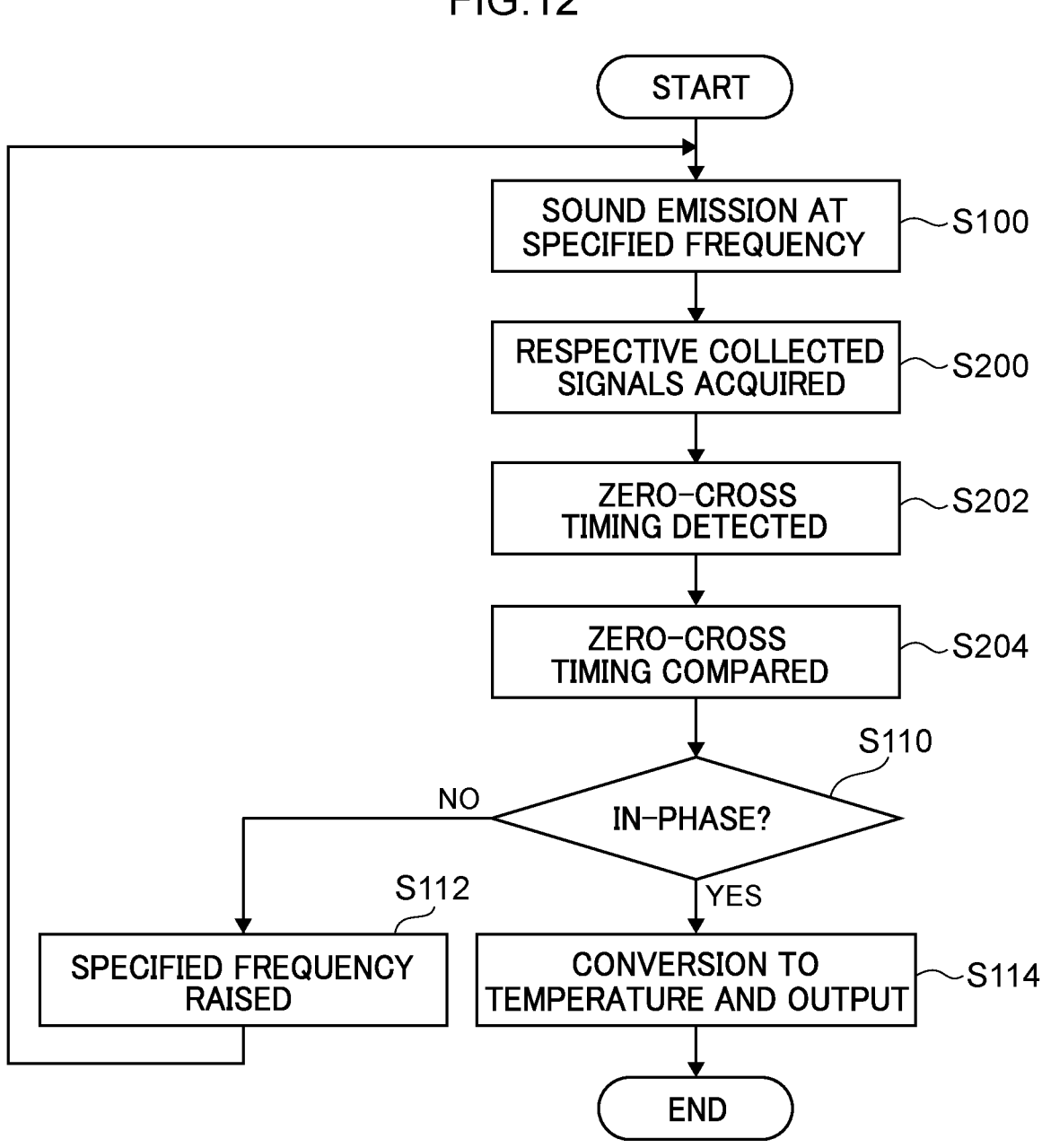
FIG. 12 is a flow chart showing details of temperature measurement processing by the headset according to the second embodiment of the technique of the present disclosure.

Operation of Headset According to Second Embodiment of Technique of Present Disclosure When the housing 10 of the headset 200 is worn at the user's ear and an instruction for temperature measurement is received from the user's terminal (not shown) by wireless communication, temperature measurement processing as shown in FIG. 12 is executed by the computation unit 222. The same reference numerals are assigned to the same processing as in the first embodiment, and detailed description thereof is omitted.

First, in step S100, the reproduction unit 20 is controlled such that a measurement signal that changes at any one of plural predetermined frequencies is output from the driver 14.

In step S200, the first collected sound signal acquisition unit 232 acquires the collected sound signal collected by the microphone 218A. The second collected sound signal acquisition unit 234 acquires the collected sound signal collected by the microphone 218B.

In step S202, the frequency designation unit 236 detects zero-cross timing at a given location for each of the collected sound signals acquired by the first collected sound signal acquisition unit 232 and the second collected sound signal acquisition unit 234.

In step S204, if the absolute value of the difference in zero-cross timing detected in step S202 is equal to or less than a threshold value, the frequency designation unit 236 determines that the signals are in-phase, and if it is larger than the threshold value, determines that they are out of phase.

In step S110, the frequency designation unit 236 determines whether or not the signals have been determined to be in-phase, and in a case in which it has been determined that they are in-phase, the processing proceeds to step S114, while if, on the other hand, it has been determined that they are out of phase, the processing proceeds to step S112.

In step S112, a frequency that is one increment higher among the plural frequencies is set as the frequency of the measurement signal.

In step S114, the temperature conversion unit 38 measures the temperature inside the ear canal from the frequencies determined to be in-phase in step S204 described above, using the correlation between the frequency and the temperature obtained in advance. The temperature conversion unit 38 outputs the temperature measurement result via the output unit 23, and terminates the temperature measurement processing.

As explained above, the headset according to the second embodiment of the technique of the present disclosure measures the temperature inside the ear canal based on the collected sound signals collected by plural microphones when a measurement signal is output from the driver. As a result, it is possible to measure the temperature in the ear canal with high accuracy with a simple configuration.

In the above-described embodiment, the frequency at which the collected sound signals acquired by the first collected sound signal acquisition unit 232 and the second collected sound signal acquisition unit 234 correspond to an antiphase may be specified and the temperature inside the ear canal may be measured from the specified frequencies using a pre-determined correlation between frequency and temperature. For example, in a case in which the absolute value of the difference between the zero-cross timing difference in the collected sound signals acquired by the first collected sound signal acquisition unit 232 and the second collected sound signal acquisition unit 234, and ½ of the period corresponding to the frequency, is below a threshold value, it may be determined that the signals are in antiphase.

Further, the frequency designation unit 236 may specify a frequency at which, among plural frequencies, a resultant value of subtraction of the collected signals collected by the microphones 218A, 218B becomes the smallest. Further, the temperature conversion unit 38 may measure the temperature in the ear canal from the specified frequency using a pre-determined correlation between frequency and temperature.

Figure 13:
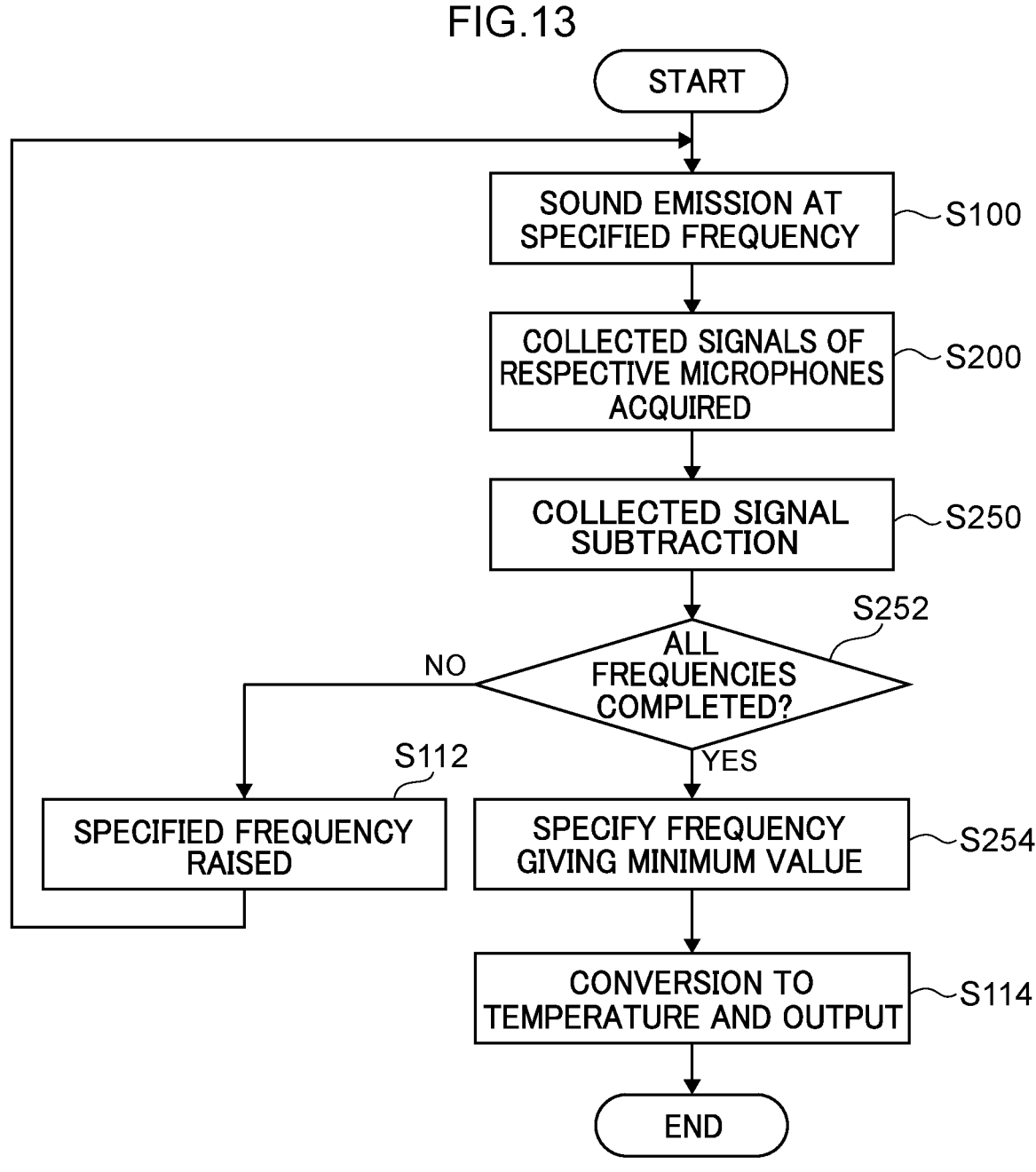
FIG. 13 is a flowchart showing details of temperature measurement processing by a headset according to another example of the second embodiment of the technique of the present disclosure.

In this case, temperature measurement processing as shown in FIG. 13 is executed by the computation unit 222. Here, the same reference numerals are assigned to the same processes as the temperature measurement processing shown in FIG. 12, and detailed description thereof is omitted.

First, in step S100, the reproduction unit 20 is controlled such that a measurement signal that changes at any one of plural predetermined frequencies is output from the driver 14.

In step S200, the first collected sound signal acquisition unit 232 acquires the collected sound signal collected by the microphone 218A. The second collected sound signal acquisition unit 234 acquires the collected sound signal collected by the microphone 218B.

In step S250, the frequency designation unit 236 calculates a signal obtained by subtracting the collected sound signal acquired by the second collected sound signal acquisition unit 234 from the collected sound signal acquired by the first collected sound signal acquisition unit 232.

In step S252, the frequency designation unit 236 determines whether or not the respective processing of the above-described steps S100, S200 and S250 has been executed with all of the plural frequencies as the frequency of the measurement signal. In a case in which the above-described steps S100, S200 and S250 have been executed with all of the plural frequencies as the frequency of the measurement signal, the processing proceeds to step S254. However, in a case in which there is a frequency among the plural frequencies for which the processing of steps S100, S200 and S250 has not been performed, the processing proceeds to step S112.

In step S112, a frequency that is one increment higher among the plural frequencies is set as the frequency of the measurement signal.

In step S254, the frequency designation unit 236 specifies, among the plural frequencies, the frequency at which the signal of the subtraction result is the minimum based on the subtraction result signal calculated in step S250.

In step S114, the temperature conversion unit 38 measures the temperature inside the ear canal using the correlation between the frequency and the temperature obtained in advance, from the frequency specified in step S254 described above, and outputs the temperature measurement result via the output unit 23, and terminates the temperature measurement processing.

Configuration of Headset According to Third Embodiment of Technique of Present Disclosure Next, a headset according to a third embodiment will be described. Parts having the same configuration as in the first embodiment are denoted by the same reference numerals, and descriptions thereof are omitted.

The third embodiment differs from the first embodiment in that the microphone simultaneously collects signals propagated along different paths and measures the temperature in the ear canal using the collected sound signals.

Figure 14:
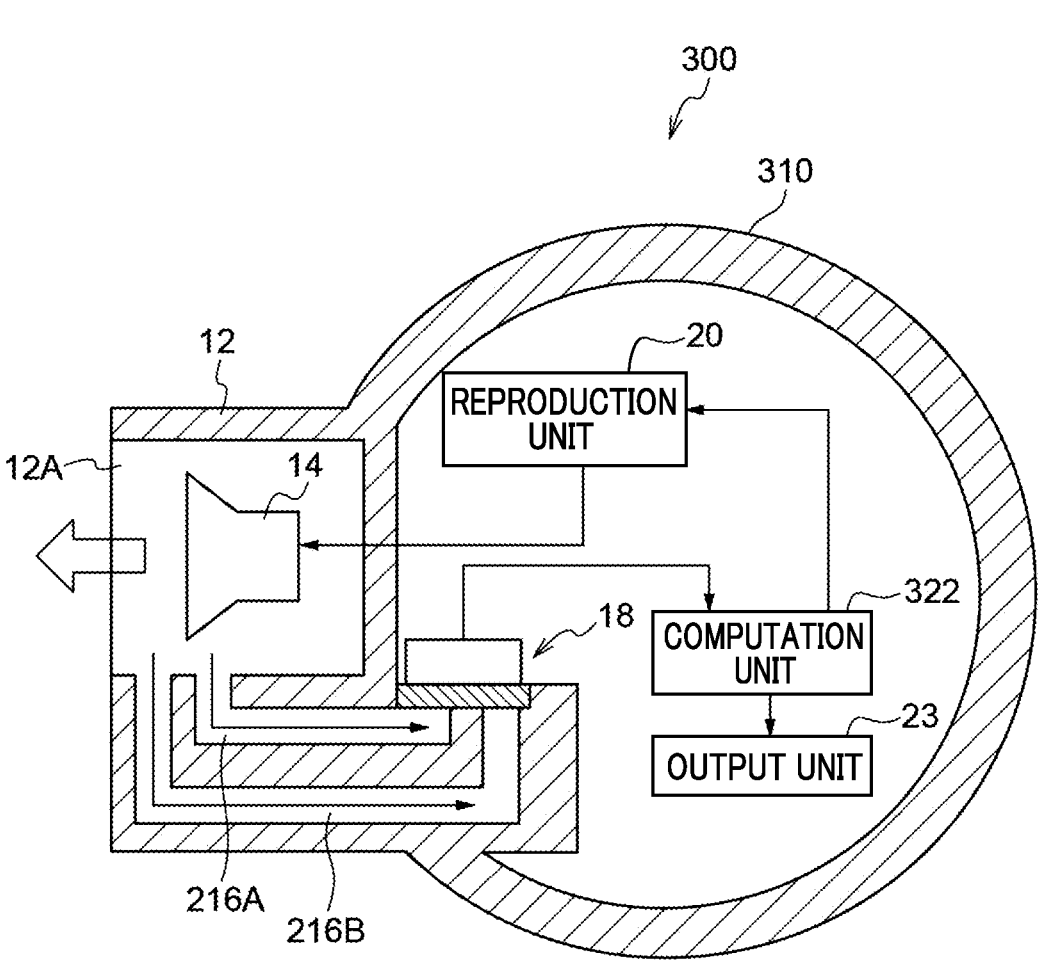
FIG. 14 is a cross-sectional view showing the overall configuration of a headset according to a third embodiment of the technique of the present disclosure.

As shown in FIG. 14, a housing 310 of headset 300 according to the third embodiment of the technique of the present disclosure has a second hollow portion 216A and a third hollow portion 216B extending from the inside of the ear canal-insertion portion 12, which are different hollow portions from the first hollow portion 12A propagating inside the ear canal-insertion portion 12. The second hollow portion 216A and the third hollow portion 216B respectively have different lengths from the ear canal insertion portion 12 to the microphone 18.

A microphone 18 is provided to simultaneously collect signals propagating through the second hollow portion 216A and the third hollow portion 216B.

A computation unit 322 measures the temperature inside the ear canal based on the collected sound signals collected by the microphone 18 when a measurement signal is output from the driver.

Figure 15:
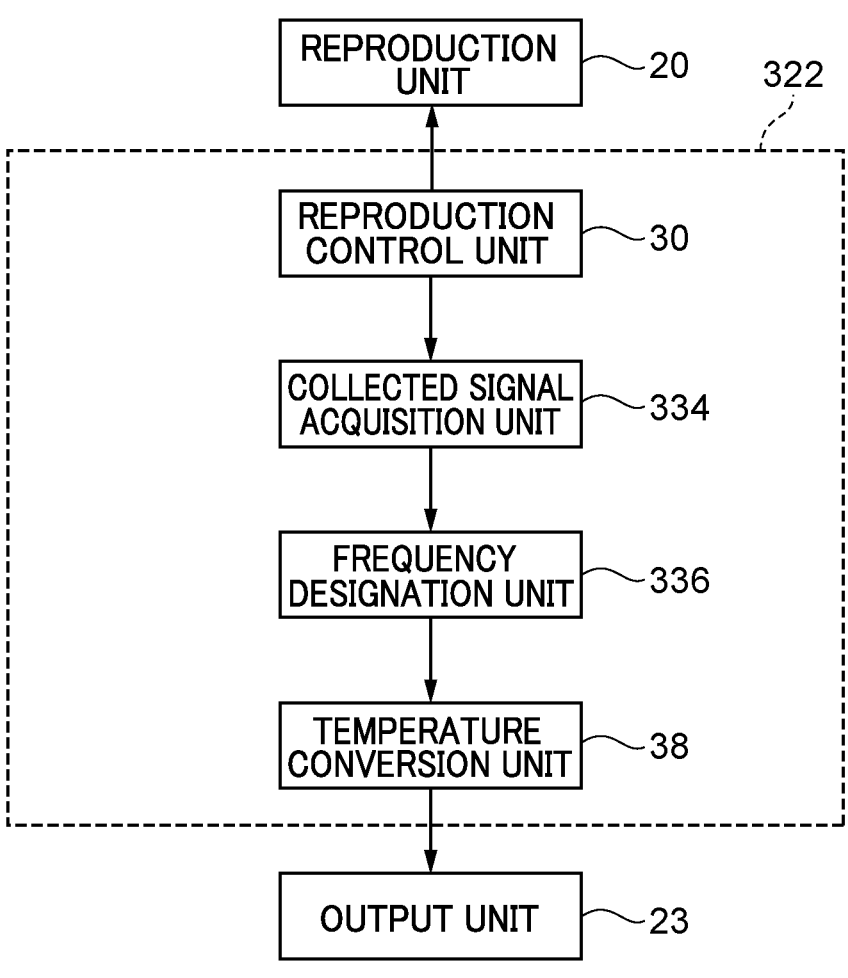
FIG. 15 is a block diagram showing a computation unit of the headset according to the third embodiment of the technique of the present disclosure.

Specifically, the computation unit 322 functionally includes, as shown in FIG. 15, a reproduction control unit, a collected sound signal acquisition unit 334, a frequency designation unit 336 and a temperature conversion unit 38.

The collected sound signal acquisition unit 334 acquires the collected sound signals collected by the microphone 18.

The frequency designation unit 336 specifies the frequency at which the collected sound signal obtained by the collected sound signal obtaining unit 334 is the smallest, from among plural predetermined frequencies.

The temperature conversion unit 38 measures the temperature inside the ear canal from the specified frequencies using a pre-determined correlation between frequency and temperature. The temperature conversion unit 38 outputs the temperature measurement result via the output unit 23.

Figure 16:
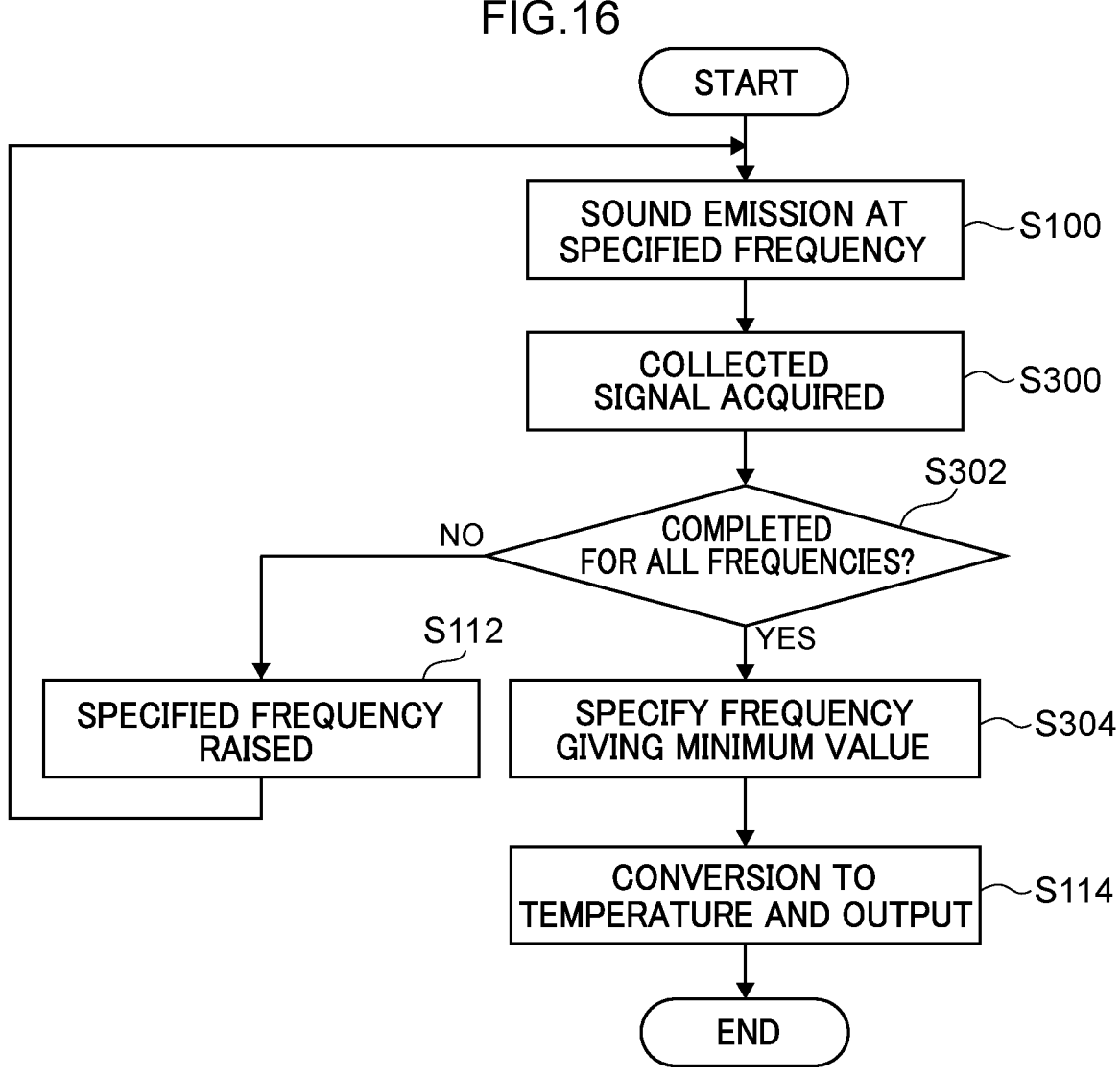
FIG. 16 is a flow chart showing details of temperature measurement processing by the headset according to the third embodiment of the technique of the present disclosure.

Operation of Headset According to Third Embodiment of Technique of Present Disclosure When the housing 310 of the headset 300 is worn at the user's ear and an instruction for temperature measurement is received from the user's terminal (not shown) by wireless communication, temperature measurement processing as shown in FIG. 16 is executed by the computation unit 322.

First, in step S100, the reproduction unit 20 is controlled such that a measurement signal that changes at any one of plural predetermined frequencies is output from the driver 14.

In step S300, the collected sound signal acquisition unit 334 acquires the collected sound signals collected by the microphone 18.

In step S302, the frequency designation unit 336 determines whether or not the respective processing of the above-described steps S100 and S300 has been executed with all of the plural frequencies as the frequency of the measurement signal. In a case in which the above-described steps S100 and S300 have been executed with all of the plural frequencies as the frequency of the measurement signal, the processing proceeds to step S304. However, in a case in which there is a frequency among the plural frequencies for which the processing of steps S100 and S300 has not been performed, the processing proceeds to step S112.

In step S112, a frequency that is one increment higher among the plural frequencies is set as the frequency of the measurement signal.

In step S304, the frequency designation unit 336 specifies the frequency, among the plural frequencies, at which the collected sound signals become the smallest based on the collected sound signals acquired in step S300.

In step S114, the temperature conversion unit 38 measures the temperature inside the ear canal from the frequency specified in step S304 described above, using the correlation between the frequency and the temperature obtained in advance.

The temperature conversion unit 38 outputs the temperature measurement result via the output unit 23, and terminates the temperature measurement processing.

As explained above, the headset according to the third embodiment of the technique of the present disclosure measures the temperature inside the ear canal based on the collected sound signals collected by the microphone when a measurement signal is output from the driver. As a result, it is possible to measure the temperature in the ear canal with high accuracy with a simple configuration.

In the above-described embodiment, the temperature inside the ear canal may be measured by specifying the frequency at which the collected sound signal acquired by the collected sound signal acquisition unit 334 becomes the largest from the specified frequencies using a pre-determined correlation between frequency and temperature.

EXAMPLES

Figure 17:
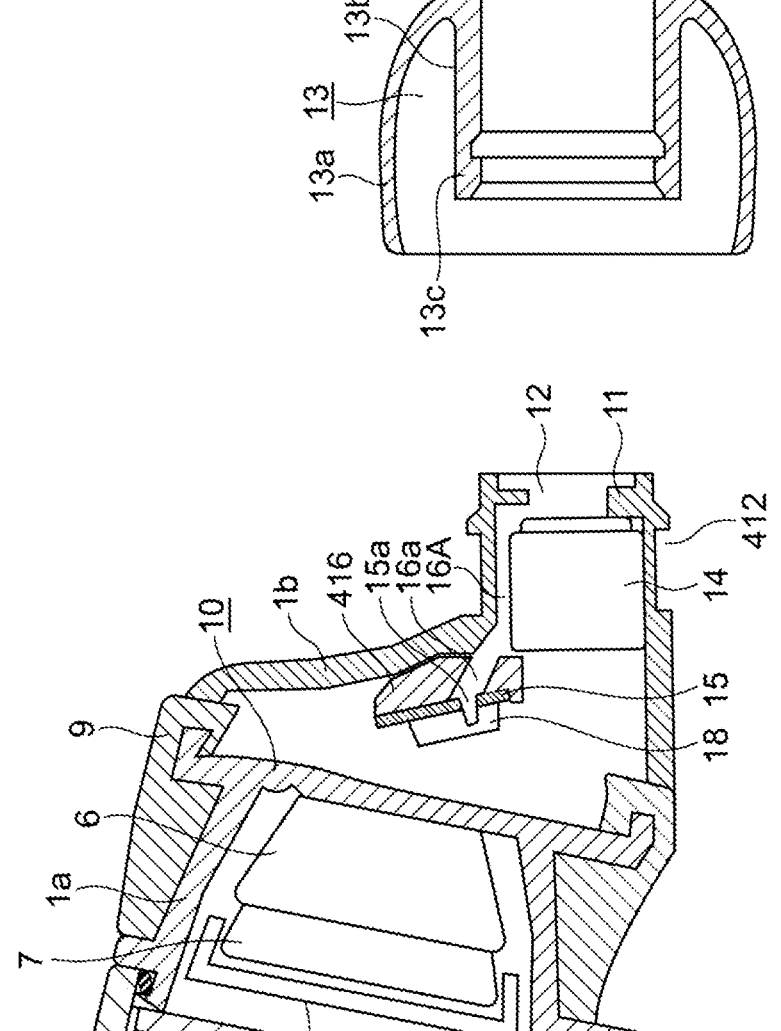
FIG. 17 is a cross-sectional view showing the overall configuration of the headset according to an example.

An example of the headset according to the first embodiment is explained. As shown in FIG. 17, the housing 10 of the headset of this embodiment is formed by fitting together a main housing 1a and a front housing 1b.

The main housing 1a is a hollow-shaped member having a cylindrical shape as a whole, and having a rearward opening that is closed by a cover 2. A printed wiring board 3 is arranged inside the main housing 1a so as to face the opening. The printed wiring board 3 is a board on which electronic components functioning as the reproduction unit 20, the computation unit 22, and the output unit 23 are mounted.

A battery 6 is arranged in front of the printed wiring board 3 with a battery cushion 7 and a battery cap 8 interposed therebetween.

As shown in FIG. 17, a housing rubber 9 is provided at the outer periphery of the main housing 1a. The housing rubber 9 is a cylindrical elastic member fitted around the outer periphery of the main housing 1a, which buffers contact with the ear and prevents water from entering the housing 10.

As shown in FIGS. 17 and 18, the front housing 1b is arranged so as to close off the front opening of the cylindrical main housing 1a. The front housing 1b has an oblique truncated cone shape as a whole, and a part of the peripheral edge is slightly raised toward the eardrum side.

An ear canal insertion portion 12 is provided in front of the front housing 1b and protrudes from the top of the oblique truncated cone toward the eardrum side. The ear canal insertion part 12 has a cylindrical shape provided in a part of the front housing 1b, and both the front and the rear are opened, whereby the inside and outside of the front housing 1b are communicated with each other. A driver 14 having a cylindrical case is installed inside the ear canal insertion portion 12. Therefore, a positioning portion 11 for the driver 14 is provided in the vicinity of the front opening of the ear canal insertion portion 12, and by engaging the front end of the driver 14 with the positioning portion 11, the driver 14 is fixed to the inner surface of the ear canal insertion portion 12. The rear end of the driver 14 is positioned near the front end of the front housing 1b. The driver 14 has a magnetic circuit for generating an output signal, a diaphragm, and the like in a cylindrical case, and has an appropriate well-known structure.

As shown in FIG. 18, a lead wire 414 is arrayed from behind the driver 14. The lead wire 414 is connected to the printed wiring board 3.

The headset of the present embodiment has a microphone 18. The microphone 18 is provided in the vicinity of the ear canal insertion portion 12 in the front housing 1b; that is, rearward of the driver 14.

As shown in FIGS. 17 and 18, the microphone 18 is mounted on a microphone board 15. The microphone board 15 is fixed to a block 416. The block 416 is a block-shaped member that supports the microphone 18 and the microphone board 15. The microphone board 15 and the block 416 are provided with openings 15a and 16a so that the sounds signals in the ear canal can reach the microphone 18.

Although illustration is omitted from FIG. 17, a pressure sensitive adhesive 17 is provided between the microphone 18 and the block 416 and between the block 416 and the front housing 1b, respectively, to secure them together. The pressure sensitive adhesive 17 is provided with an opening 17a so as not to block the second hollow portion 16A or the opening 15a of the microphone board 15.

Figure 19:
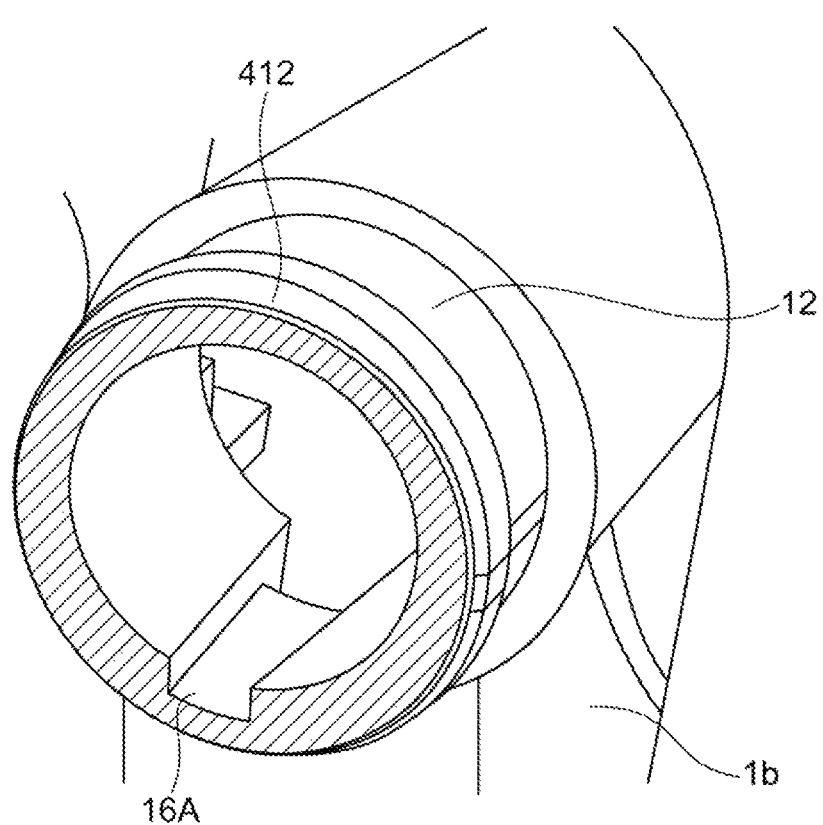
FIG. 19 is an enlarged perspective view of the ear canal-insertion part in the example.

As shown in FIGS. 17 and 19, the inner surface of the ear canal insertion portion 12 is provided with a second hollow portion 16A that is a groove formed along the axial direction of the ear canal-insertion portion 12. FIG. 19 is a cross-sectional view of the ear canal insertion portion 12 at an earpiece attachment groove 412. The second hollow portion 16A is a rectangular groove-shaped space formed between side surfaces of the driver 14, and the front end of the ear canal insertion portion 12 is communicated with the opening 16a of the block 416 fixed to the front housing 1b.

As shown in FIGS. 17 and 18, an earpiece 13 is fixed to the outer periphery of the ear canal insertion portion 12. The earpiece 13 is also called an eartip, an earpad, or an earcap, and consists of an elastic member such as silicone rubber. The earpiece 13 has, at the tip of a cylindrical portion 13b fitted to the outer periphery of the ear canal insertion portion 12, a portion 13a that is formed in a hemisphere and adheres to the wall surface of the ear canal. As shown in FIGS. 18 and 19, an earpiece attachment groove 412 is provided at the outer periphery of the ear canal insertion portion 12. However, as shown in FIG. 17, a fitting portion 13c is provided at the inner periphery of the cylindrical portion 13b of the earpiece 13. The earpiece 13 is fixed to the ear canal insertion portion 12 by engagement of the fitting portion 13c with the earpiece attachment groove 412.

The technique of the present disclosure is not limited to the above-described embodiments, and various modifications and applications are possible within a range that does not depart from the gist of the technique of the present disclosure.

For example, in the first and second embodiments described above, when measurement signals that change at plural frequencies are output at the same time, signals acquired in two systems may be added or subtracted and frequency analysis used to determine which frequency bands are to be canceled. Then, conversion to temperature may be performed using a table or formula storing the correlation between frequency and temperature measured or simulated in advance in a similar system. Further, white noise may be used as the measurement signal.

Further, a case in which the driver is arranged in the ear canal insertion portion has been described as an example, but the present invention is not limited to this. The driver may be placed at any other position as long as it is a position that can output the measurement signal into the ear canal insertion portion.

Further, a non-audible band may be used as the frequency of the measurement signal. In this case, the temperature in the ear canal may be measured by adding the measurement signal to music or the like to which the user is listening.

All publications, patent applications and technical standards mentioned herein are incorporated herein by reference to the same extent as if each individual publication, patent application and technical standard were specifically and individually indicated to be incorporated by reference.

The invention claimed is:

1. A headset for use by being worn at an ear of a user comprising:
   a hollow housing;
   a cylindrical ear canal insertion part that is a portion of the housing, and that is adapted to be inserted into an ear canal of the user when the headset is worn by the user;
   a driver for signal output, provided at an interior of the housing;
   a first hollow part provided inside the ear canal insertion part, through which a signal output from the driver propagates;
   a second hollow part that is different from the first hollow part, extending from inside the ear canal insertion part, the second hollow part including a space formed between an inner surface of the ear canal insertion part and the driver;
   a microphone provided so as to collect a signal propagating at the second hollow part; and
   a computation unit configured to measure a temperature inside the ear canal of the user when the headset is worn by a user based on a collected signal collected by the microphone at a time at which a measurement signal is output from the driver,
   wherein the computation unit measures the temperature inside the ear canal of the user based on the measurement signal output from the driver and the collected signal collected by the microphone,
   wherein the driver sequentially outputs the measurement signal that changes at each of a plurality of predetermined frequencies, and
   wherein the computation unit specifies, from among the plurality of predetermined frequencies, a frequency at which the measurement signal output from the driver and the collected signal collected by the microphone exhibit a predetermined relationship, and measures the temperature inside the ear canal of the user from the specified frequency using a predetermined correspondence between the frequency and the temperature.

2. The headset according to claim 1, wherein the predetermined relationship is a relationship corresponding to an in-phase correlation or an antiphase correlation between the measurement signal output from the driver and the collected signal collected by the microphone.

3. The headset according to claim 1, wherein the predetermined relationship is a relationship in which an addition or subtraction result of the measurement signal output from the driver and the collected signal collected by the microphone becomes a maximum value or a minimum value.

4. The headset according to claim 1, wherein the second hollow part includes a groove formed along an axial direction of the ear canal insertion part.

5. A headset for use by being worn at an ear of a user, comprising:
   a hollow housing;
   a cylindrical ear canal insertion part that is a portion of the housing, and that is adapted to be inserted into the ear canal of the user when the headset is worn by the user;

a driver for signal output, provided at an interior of the housing;

a first hollow part provided inside the ear canal insertion part, through which a signal output from the driver propagates;

a second hollow part that is different from the first hollow part, extending from inside the ear canal insertion part, the second hollow part including a space formed between an inner surface of the ear canal insertion part and the driver;

a plurality of microphones provided at positions separated from each other so as to collect signals propagating at the second hollow part; and a computation unit configured to measure a temperature inside the ear canal of the user based on a collected signal collected by the microphone at a time at which a measurement signal is output from the driver, wherein the driver sequentially outputs the measurement signal that changes at each of a plurality of predetermined frequencies, and wherein the computation unit specifies, from among the plurality of predetermined frequencies, a frequency at which the collected signals collected by each of the plurality of microphones exhibit a predetermined relationship, and measures the temperature inside the ear canal of the user from the specified frequency using a predetermined correspondence between the frequency and the temperature.

6. The headset according to claim 5, wherein the predetermined relationship is a relationship corresponding to an in-phase correlation or an antiphase correlation among the collected signals collected by each of the plurality of microphones.

7. The headset according to claim 5, wherein the predetermined relationship is a relationship in which an addition or subtraction result of the collected signals collected by each of the plurality of microphones becomes a maximum value or a minimum value.

8. The headset according to claim 5, wherein the second hollow part includes a groove formed along an axial direction of the ear canal insertion part.

9. A headset for use by being worn at an ear of a user, comprising:

a hollow housing;

a cylindrical ear canal insertion part that is a portion of the housing, and that is adapted to be inserted into an ear canal of the user when the headset is worn by the user;

a driver for signal output, provided at an interior of the housing;

a first hollow part provided inside the ear canal insertion part, through which a signal output from the driver propagates;

a second hollow part that is different from the first hollow part, extending from inside the ear canal insertion part, the second hollow part including a space formed between an inner surface of the ear canal insertion part and the driver;

a third hollow part that is different from the first hollow part and the second hollow part, extending from inside the ear canal insertion part;

a microphone provided so as to collect a signal propagating at the second hollow part and a signal propagating at the third hollow part; and a computation unit configured to measure a temperature inside the ear canal based on a collected signal collected by the microphone at a time at which a measurement signal is output from the driver, wherein the driver sequentially outputs the measurement signal that changes at each of a plurality of predetermined frequencies, and wherein the computation unit specifies, from among the plurality of predetermined frequencies, a frequency at which the collected signal collected by the microphone becomes a maximum value or a minimum value, and measures the temperature inside the ear canal of the user from the specified frequency using a predetermined correspondence between the frequency and the temperature.

10. The headset according to claim 9, wherein the second hollow part includes a groove formed along an axial direction of the ear canal insertion part.

* * * * *